United States Patent [19]

Swartz

[11] 4,243,751

[45] Jan. 6, 1981

[54] ELECTROCHEMICAL PROCESS AND APPARATUS TO CONTROL THE CHEMICAL STATE OF A MATERIAL

[75] Inventor: Mitchell R. Swartz, Malden, Mass.

[73] Assignee: Massachusetts Institute of Technology, Cambridge, Mass.

[21] Appl. No.: 911,625

[22] Filed: Jun. 1, 1978

Related U.S. Application Data

[62] Division of Ser. No. 636,290, Nov. 28, 1975, Pat. No. 4,139,348.

[51] Int. Cl.³ .................. G01N 27/26; G01N 27/28; G01N 33/16; A61B 10/00
[52] U.S. Cl. .................. 435/168; 23/232 E; 23/230 R; 47/1.4; 204/1 T; 204/195 R; 204/195 B; 204/180 B; 356/40; 356/41; 422/83; 422/98; 422/186; 435/173
[58] Field of Search ............ 47/1.4; 195/103.5 R, 195/127, DIG. 11; 356/40, 41; 422/98, 186, 83; 23/232 E, 230 R; 204/1 P, 1 S, 1 T, 1 Y, 73, 160, 195 R, 195 T, 158, 180 B, 180 P, 195 B, 195 S; 435/168, 173

[56] References Cited

U.S. PATENT DOCUMENTS

| 3,036,895 | 5/1962 | Cole | 23/232 E |
|---|---|---|---|
| 3,243,918 | 4/1966 | Machiedo et al. | 47/1.4 |
| 3,430,050 | 2/1969 | Grimmeis | 357/40 |
| 3,723,062 | 3/1973 | Dahms | 204/195 T X |
| 3,873,267 | 3/1975 | Swartz | 23/230 B |
| 3,975,238 | 8/1976 | Bean et al. | 195/103.5 R |
| 4,139,348 | 2/1979 | Swartz | 23/232 E |

FOREIGN PATENT DOCUMENTS 482187 11/1975 U.S.S.R. .

OTHER PUBLICATIONS

Kocholaty; Detoxification of Crotalus Atrox Venom by Photoxidation in Presence of Methylene Blue, Toxicon, 1966, vol. 3, pp. 175-186.

Hydrogen Evol. by Nitrogen-Fixing Arabaena Cylindrical Cultures; Science, vol. 184, pp. 174-175, Benemann et al.

*Primary Examiner*—Michael S. Marcus
*Attorney, Agent, or Firm*—Arthur A. Smith, Jr.; Robert Shaw; Anthony M. Lorusso

[57] ABSTRACT

Electrochemical process and apparatus to control the chemical state of a material, that is, to cause said material to retain desired characteristics in an environment that normally would cause a change in those characteristics or to cause a material that has deteriorated from a desired chemical state to revert to the desired state.

30 Claims, 14 Drawing Figures

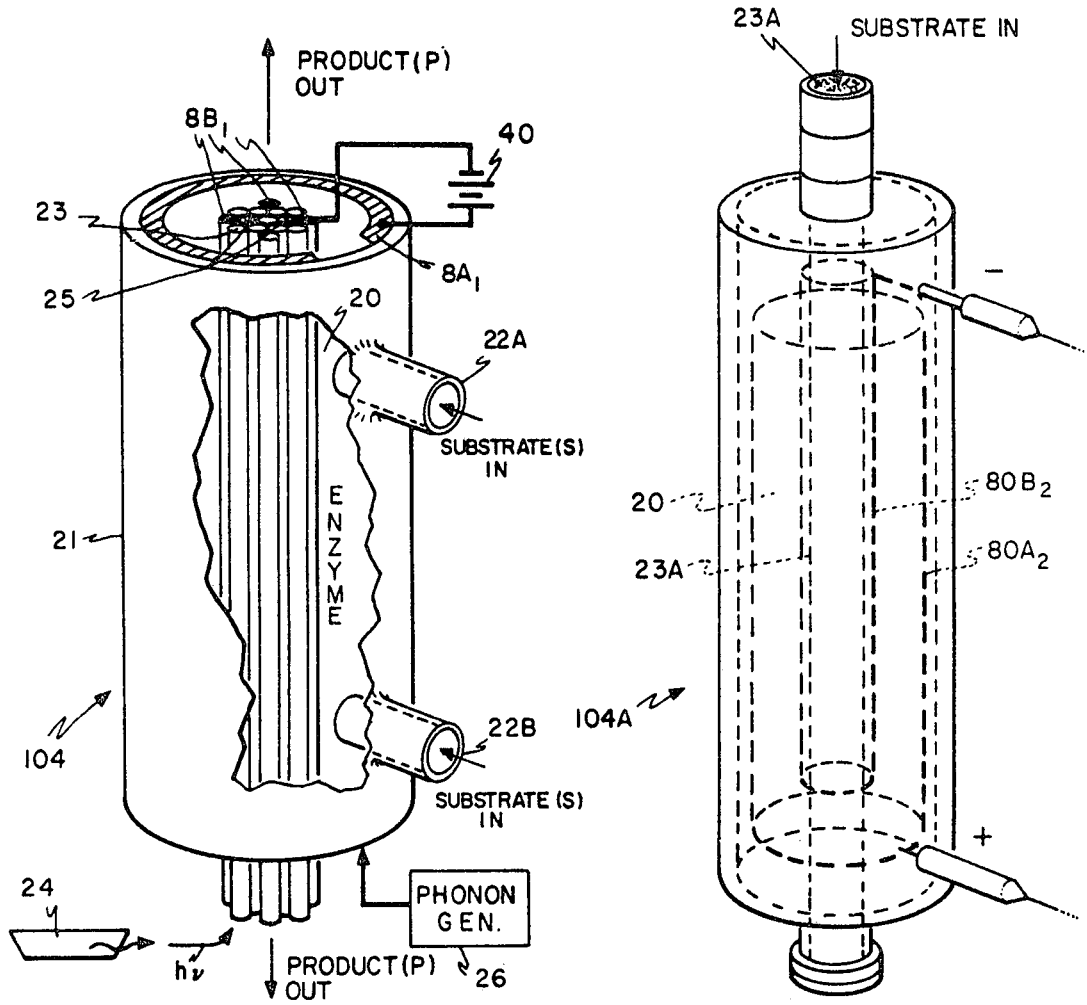
FIG. 8
FIG. 9
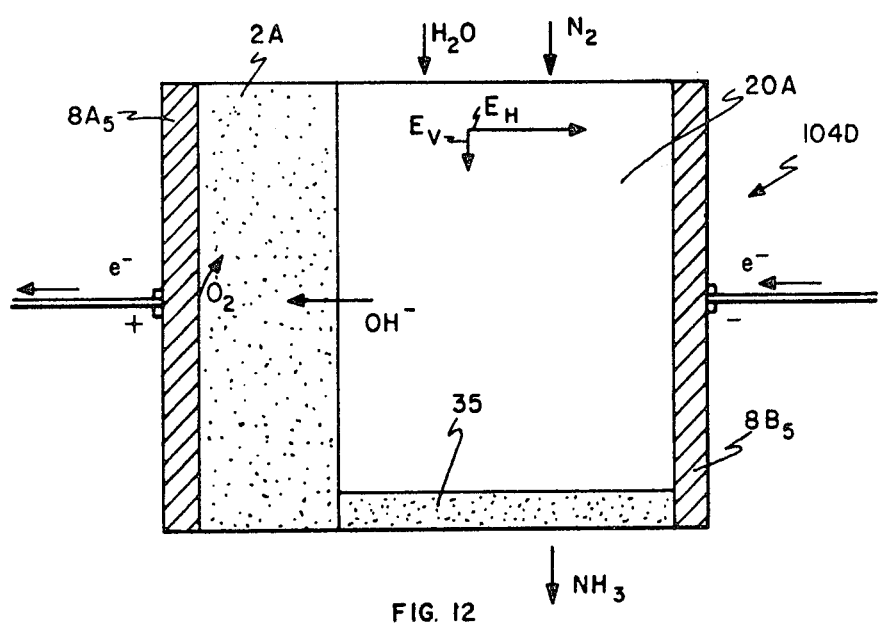
FIG. 12

ELECTROCHEMICAL PROCESS AND APPARATUS TO CONTROL THE CHEMICAL STATE OF A MATERIAL

This is a division of application Ser. No. 636,290 now U.S. Pat. No. 4,139,348, filed Nov. 28, 1975 and is being filed to comply with a requirement for restriction.

The present invention relates to electrochemical processes and apparatus for controlling the chemical state of a material.

By way of background and to place reasonable limits on the size of this disclosure, the following publications are noted: *Handbook of Biochemistry*, second edition, published by Plenum Press, 1973, containing papers delivered at an American Chemical Society Symposium, Chicago, 1973 and, in particular, the paper entitled "The Evolution of Metals as Essential Elements [with special reference to iron and copper" by Frieden at pp. 1-30; *Biochemistry*, Lehninger, published by Worth, Inc., 1970, pp. 148-150; "Methemoglobin," Conant et al (1924), *The Journal of Biological Chemistry*, Vol. LXII, No. 3, pp. 595-620; "*Oxidation-Reduction Potentials of the Methemoglobin-Hemoglobin System,*" Taylor et al (1939), published in *The Journal of Biological Chemistry*, pp. 649-622; *The Pharmacological Basis of Therapeutics*, of the edition published by MacMillan and Company (1970), pp. 1056-7 and 166a; *The Red Cell* (Harris et al), p. 486, published by Harvard University Press (1970); "Emphores," Pardee, pp. 216 et seq. of *Structure of Chemical and Molecular Biology*, edited by Rich et al, published by Freeman, Inc. (1968); *Advanced Inorganic Chemistry*, Cotton et al, pp. 403-421 and 801-1055, published by Wiley, Interscience (1972); *Current Drug Handbook*, pp. 74-76, published by Saunders Company (1974); and *Introduction to A Submolecular Biology*, Szent-Gyorgi, Academic Press (1960).

The invention is multi-faceted. A common thread is that of renewing or rejuvenating materials that have for one reason or another changed (or would change in the absence of countermeasures) to an undesired state from a desired state. Accordingly, the principal object of the invention is to provide a system containing a material that is subject to a chemical change, but in which the chemical state of the material is controlled.

One aspect of the invention is concerned with the detection of certain molecular species wherein a material characteristic such as, for example, its opacity at a single wavelength or its color, is changed as a consequence of a chemical reaction that occurs in the presence of a molecular species of interest. A further object, therefore, is to provide a molecular species detector wherein changes in characteristics of a material are effected in the presence of a molecular species of interest and such changes are sensed to determine the presence of the species and the amount of that species of molecule present.

In such a detector the chemical reaction that changes the material characteristic of interest has a relatively short time constant ($\tau_c$ herein); there is also a chemical deterioration of the material over a longer period of time ($\tau_o$ herein) and in the system disclosed, that deterioration is counteracted.

Another object is to provide a molecule detector wherein said deterioration is periodically counteracted to reset the detector.

Still another object is to provide a detector of the foregoing type for in vivo use.

The literature abounds with writings delineating the need for systems for detection of $O_2$, $CO$, $CO_2$, $NO$, $NO_2$, $SO_2$, $OH^-$, $F^-$, $H_2S$, $H_2$, $HCl$, $D_2$, $CN$, etc. Such systems may be used, by way of illustration, to measure the level of pollutants in an air environment, or in the exhaust fumes of a motor vehicle, or a smokestack. There is need, as well, to measure oxygen levels or carbon monoxide levels in vivo without removing samples of blood or tissue from the body of a person; and there is need to sense the presence and the amount of other small molecules in the blood of such person.

Another object is to provide a detector which can sense the presence of a species of small molecule in a fluid environment and can give an indication of the partial pressure thereof, in the atmosphere, in vivo, and in other environments.

In certain chemical processes, precursors of a product are passed through a column containing an enzyme or other catalyst under controlled conditions; the precursors react within the column in the presence of the enzyme or other catalyst which itself undergoes an aging process.

Still another object of this invention is to provide a way to reverse the aging process of enzymes or other catalysts.

Still another object is to inactivate viruses, microbes and certain proteins.

Still another object is to provide a way to preserve a material against oxidation and/or aging, e.g., certain tissues, gametes and other biomaterials.

Still another object is to accelerate the aging process of certain materials such as, for example, microorganisms, hemoglobin (to form methemoglobin, as may be used in a cyanide detector).

Still another object is to restore chemical catalysts or reagents which age and, eventually, if left alone, cease to be functional.

Still another object is to protect materials from oxygen, e.g., biopolymers such as nitrogenase wherein oxygen inactivates the active site.

Still another object is to maintain materials in a pseudo-living state and to use them in that state for molecule detection and chemical synthesis.

These and still further objects are discussed hereinafter and are particularly delineated in the appended claims.

The objects are achieved in a process wherein a chemical change wrought upon a material is reversed by injecting appropriate electrical charge carriers into the material to counteract unwanted deterioration thereof and cause the material to revert to a desired state; or the injection of such carriers can be effective to maintain the desired state of a material that would otherwise undergo chemical change.

The invention is hereinafter explained with reference to the accompanying drawing in which:

FIG. 8 is an isometric section view, partly cutaway and diagrammatic in form, showing one section of a catalytic system wherein a substrate is reacted in the presence of a catalyst to provide a product, the catalyst being resettable in the same manner as is the material in the system of FIG. 1;

FIG. 9 is an isometric view of a modification of the section of FIG. 8;

FIG. 12 is a side section view of a further modification of the section of FIG. 8.

To avoid confusion, in this specification two phenomena that appear throughout the discussion should be distinguished. In the molecular species detector herein disclosed, one or more characteristics of a material (e.g., the optical density of the material) change in the presence of the molecular species of interest; that change in characteristics occurs because of what is termed herein a chemical "reversible binding" and is an effect having a short time constant ($\tau_c$). There is another effect that is long range (i.e., characterized by a typically long time constant ($\tau_o$) and is referred to throughout this specification as "deterioration"; deterioration is a degrading effect upon the material by virtue of the environment within which the material is placed, leading to progressive insensitivity toward the species of interest. Thus, with respect to the molecular species detector hereinafter described the term "reversible binding" refers to the reversible chemical binding, e.g., oxygenation, between the species of interest and the active material of the detector (e.g. the formation of oxygenated hemoglobin (i.e., oxyhemoglobin) when the material is hemoglobin) whereas deterioration is a long range opacity that set in because of the environment (e.g., the formation of $Fe^{+++}$ due to the oxidation of the hemoglobin). The reversible binding, e.g., oxygenation, effect is a direct function of the partial pressure or amount of the species of interest in the vicinity of the sensing material and the material reverts to its original state if the species of interest is removed in direct proportion to the amount removed. The deterioration effect does not revert just because the species of interest is removed. In the enzyme catalytic system later described, "reaction" refers to the actions upon a substrate to produce a product, whereas "deterioration" refers to degradation of the enzyme due, in part, to the catalytic reaction but also to the environment in general.

Figure 1:
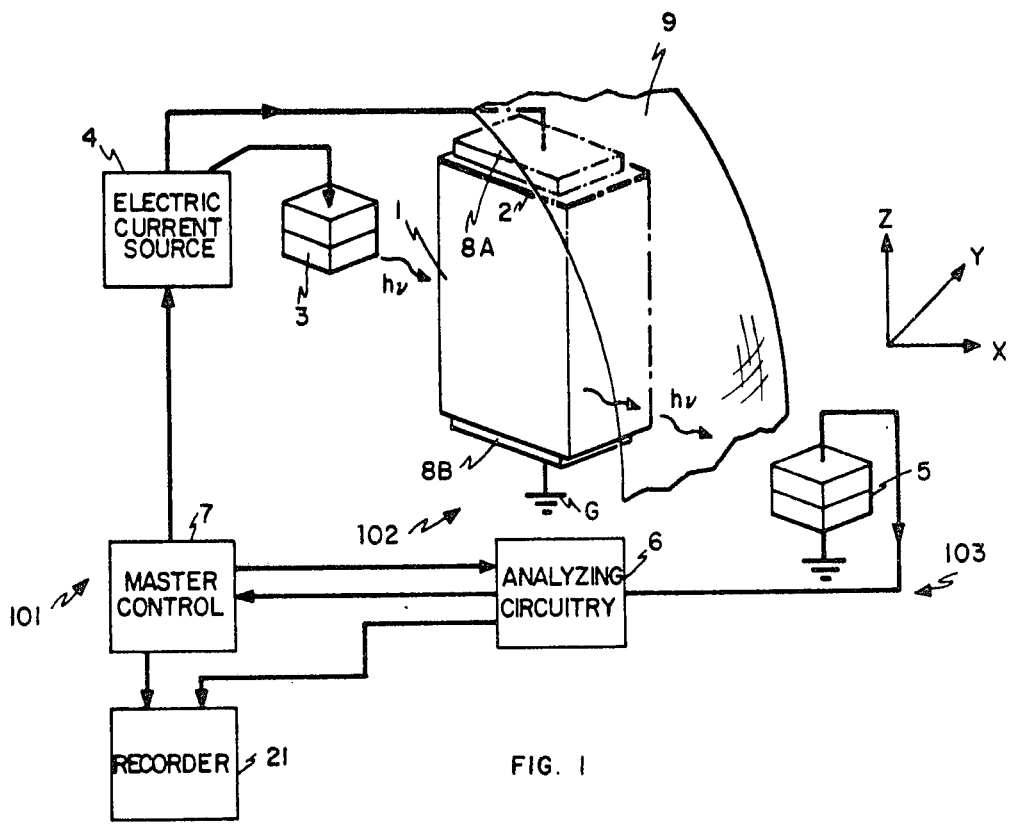
FIG. 1 is a schematic representation, partly block diagram in form, showing a resettable detector system to sense the partial pressure of a molecular species in a fluid and includes a radiation source and radiation sensor, two electrodes and a material through which the radiation passes and which modifies the radiation.
Figure 2:
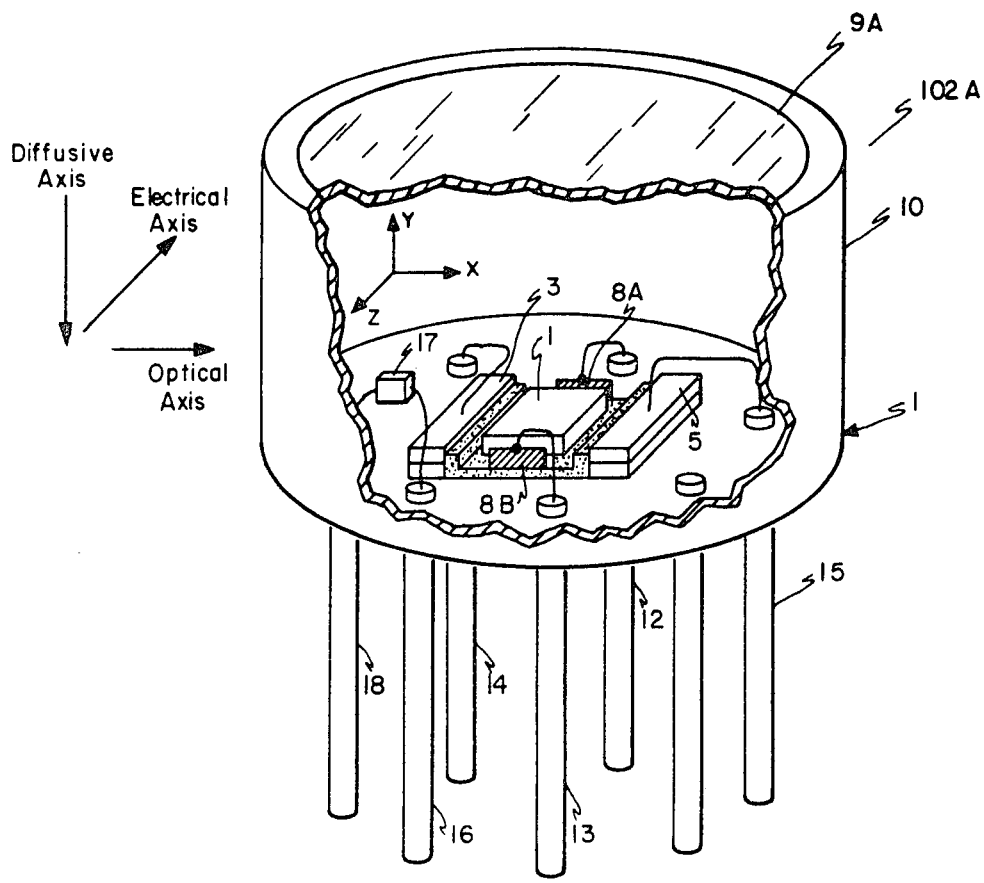
FIG. 2 is an enlarged isometric view, partly cutaway, showing a practical embodiment of a molecular species detector that may be used in vivo.

The apparatus shown diagrammatically at 101 in FIG. 1 is a molecular species detector system which senses the partial pressure of a molecular species in a fluid environment. The detector system 101 comprises a device 102 that includes a radiation-transmitting material 1 whose optical density changes at specific wavelengths of electromagnetic radiation when said material is exposed to the molecular species of interest, by virtue of reversible binding of the molecules of the species. A light emitting diode or other radiation source 3, energized by a current source 4, generates radiation at a predetermined frequency and that radiation passes through the material 1 to a radiation sensor 5 to provide a current output that bears a relationship to the intensity of radiation received. The radiation source 3, the material 1, and the radiation sensor 5, as shown in FIG. 2 and the other figures herein, form a unitary structure wherein the three elements just named bear a fixed mechanical relationship to one another in order that the output of the radiation sensor 5 be a continuous function of the intensity of the radiation received, as just noted, and not include a component due to other irrelevant factors. The electric current output of the sensor 5 is connected to electrical circuitry 103 that includes analyzing circuitry 6. Any change in the density of the material 1 as a consequence of said reversible binding results in a change in the intensity of the light striking the sensor 5, thereby causing a change in the output current of the sensor 5. The electrical circuitry 103 (which can include an appropriately calibrated ammeter) notes the current and relates it to the partial pressure of the molecular species in the fluid. (Thus, the system 101 consists of a species detector 102 that includes the material 1, the LED 3, sensor 5, etc., and the outside electrical circuitry 103.) Radiation transmission, as later explained, of the material 1 is also affected by an aging process whereby the opacity of the material increases as a function of time. Periodically, the material 1 is reset or caused to revert to its original state, as now explained with respect to a system wherein the material 1 includes an emphore, that is, the material consists of molecules which are capable of enzymatic effect upon the emphore. (See the Pardee article previously mentioned for a definition of emphores.)

More specifically, the material 1 at this juncture is a composite or resultant material that includes a gelatin binder containing hemoglobin to form a matrix material, a dye such as methylene blue that serves as an electroactive mediator, and small amounts of a plasticizer, such as glycerin to prevent drying; and the molecular species sensed is oxygen (see the accompanying writing entitled "An Oxygen Partial Pressure Sensor with Reset"). The diode 3 in an actual system is a light emitting diode (e.g., Motorola MLED-455); the LED used emits radiation at 660 to 680 nanometers. The detector is a back biased equivalent diode, but can be a photoconductor, phototransistor, photofet, or other optical detector. Hemoglobin contains the transition metal iron which is the active chemical element in the sensing system and enables the material 1 reversibly to bind small molecules. Initially, the material is red; as oxygen diffuses into it the color changes by a process of oxygenation to orange (oxyhemoglobin) and, more slowly, by oxidation, to brown (methemoglobin). The orange color results from the oxygenation process wherein the transition metal, iron, remains in the form Fe$^{++}$, where as oxidation produces methemoglobin wherein the iron is in the Fe$^{+++}$ form. The oxygen partial pressures (P$_{o2}$ herein) in the environment determines the amount of the material 1 that changes to orange and it is the determination of that amount, optically, that indicates the P$_{o2}$ level.

After some time has passed, the Fe$^{+++}$ reaches a level wherein the sensor ceases to function accurately and must be reset. Periodically (e.g., several time a day in the particular case depicted in FIG. 1 and employing hemoglobin) a master controller 7 (e.g., a microprocessor) de-energizes the analyzing circuitry 6, but not the circuitry to the LED 3, and connects the electric current source 4 across electrodes 8A (i.e., the anode) and 8B (i.e., the cathode) to pass an electric current through the material 1. Electrons thereby introduced counteract the oxidation that has occurred in the transition metal, that is, the active element or elements in the material 1. In other words, the electrons thereby introduced to the material 1 act to reduce it to its original state. The dye permits the electron transfer between the electrodes 8A and 8B and the emphore in the material 1. During the reset cycle, the diode 3 continues to radiate into the material 1 to create excited electronic levels of the dye so as to permit charge carrier transfer thereto. To place some perspective on the system just described, the voltage developed between the electrodes 8A and 8B in actual apparatus, is about three volts (this is a function of device size) to perform the reset function. The combined effect of the electroactive mediator (i.e., the dye) and the proper radiation is to permit introduction of the charge carriers to the hemoglobin at an applied electric potential difference that minimizes the electrolysis potential of the resulting material 1. As hereinafter explained, an ion exchange membrane 2 serves to create a uniformly reduced hemoglobin over most of the bulk of the composite material 1 so as to render most of the volume between the electrodes 8A and 8B effective for charge injection. The layer labeled 9 is a layer of oxygen permeable material (e.g., Teflon or Silicone) to prevent contamination of the active sensing elements. The gelatin may be commercially available product (e.g., Knox gelatin).

The system just described is useful to sense O$_2$ (~670 nanometers), CO (~815 nanometers), cyanide (~900 nanometers) and NO$_2$ (~960 nanometers). Further systems employing different active elements and different radiation frequencies can be used to detect other small molecules. The partial pressure of the molecular species just mentioned can be found in air, but it can be determined, also, when the fluid is a liquid, e.g., blood. Hence, the system 101 can function to monitor O$_2$ or CO in blood or other tissue, in vivo, the interpreting circuitry being conencted to telemetry circuitry, for example.

In the system 101 just described the gelatin serves to entrap or bind the hemoglobin; hydrophilic additives such as glycerin act as a dopant to prevent drying and, hence, minimize denaturation. The polyene catalyst methylene blue, which is an electroactive mediator in the system, as above noted, can be replaced by other dyes in some systems, and, in general, the electroactive mediator is chosen from the group consisting essentially of dyes, quinones, free transition metals and other molecules with conjugated $\pi$-electrons. The detectors can be a photo-FET or a back-biased LED or the like of appropriate frequency sensitivity, as above noted. The emphore hemoglobin is used to sense O$_2$, CN, NO$_2$ and CO; Vaska's compound (i.e., iridium bis- (triphenylphosphine) carbonyl halogen) can be used to sense SO$_2$, O$_2$, H$_2$, tetrafluoroethylene and D$_2$.

As above noted, the small molecules of greatest interest are O$_2$, CO$_2$, CN, CO, NO, NO$_2$, SO$_2$, H$_2$S, H$_2$ D$_2$, OH$^-$ and F$^-$; to function in accordance with the present teachings, the material 1 must reversibly bind to the small molecule to-be-detected. In the case of oxygen, the materials of greatest interest are oxyemphores (i.e., oxygen-binding emphores) that are taken from the group consisting essentially of iron-containing emphores (e.g., hemoglobin, hemerythrin, myoglobin, erythrocruorin, chlorocruorin, dimethylglyoxime, bis-indigo, synthetic porphyrins, capped porphyrins, etc.) copper-containing emphores (e.g., hemocyanin), nickel-containing emphores (e.g., dimethylglyoxime), cobalt-containing emphores (e.g., dihistidine, diglutamic acid, bis-salicylaldehyde ethylene diimine, diglycine, vitamin B$_{12}$, coboglobin, pentamine, etc.), iridium-containing emphores (e.g., iridium containing Vaska's compound and congeners, and cis-1, 2-bis [diphenyl phosphine] ethylene), platinum-containing emphores (e.g., platinum bis triphenyl phosphine) and manganese-containing emphores (e.g., pthallo cyanine, etc.); in the list of oxyemphores just given, the metal named is the transition metal. Other small molecules and reversibly-binding materials 1 that are used therefor, are given in the next paragraph.

For CO, a useful material 1 contains an emphore taken from the group consisting essentially of hemoglobin, iron dimethyl glyoxime, and iridium cis-1,2-bis (diphenyl phosphine) ethylene. When the small molecule is SO$_2$, HCl, H$_2$ and D$_2$, said material 1 contains an emphore taken from the group consisting essentially of iridium chlorocarbonyl bis-triphenyl phosphine, and iridium cis 1, 2-bis diphenyl phosphine ethylene and their congeners. For cyanide (CN), said material contains an emphore taken from the group consisting essentially of hemoglobin and iron dimethyl glyoxime. As for the small molecules NO, NO$_2$, F$^-$ and OH$^-$, the material 1 is one that contains hemoglobin.

The time $\tau_R$ to return the material 1 to its original state, that is, to accomplish the reset function is found from the following expression:

$$\tau_R \simeq 9.7 \cdot 10^{10} \frac{[\Sigma]}{K} \cdot \frac{1}{\eta R}$$

wherein $\Sigma$ is the molar sum of all oxidized constituents in said material, $\kappa$ is the electric current through the material in microamperes and $\eta_R$ is the efficiency of the reduction process. Ideally $\tau_R << \tau_o$, the oxidation time.

To enlarge somewhat upon the above discussion, the transition metal atoms that can be used in the system include Group VIII elements of the periodic table, copper and zinc, but metals of the lanthanide and actinide series can also be used. The deterioration mentioned can be oxidation of the transition element, as is the case above, or it can be reduction of the transition element; in the first case reset is accomplished by injecting electrons into the emphore or other matrix material and in the latter holes are injected. The binding materials that may be used include gelatin, agar, ion exchange resins, acrylimide gel, styrenes, starches, glasses, clays, methacrylates, nylons, magnetite, nickel oxides, and other polymers. The anti-dessicant substances that can be employed to prevent drying include glycerin (i.e., glycerol), dimethyl sulfoxide, trimethylamine, and ethylene glycol. Useful electroactive mediators includes dyes (e.g., methylene blue, meta-tolulene diamine indophenol, carotene), quinones, free transition metals (including free copper and zinc), and other molecules with conjugated $\pi$-electron systems, as well as other elements and complexes with $d^-$ and $f^-$ electrons capable of moving between two or more electronic states.

In addition, the material 1 can contain trace amounts of antibiotics to prevent destruction of the material from microbial growth; such antibiotics are taken from the group consisting essentially of amphotericin B, streptomycin, penicillin, mercurials, and their congeners.

As noted above, an emphore is a molecule that is capable of a reversible combination with another molecule, but there is no net chemical or enzymatic effect upon either the emphore or the other molecule which is bound. Living systems have evolved many such emphores; some reside in tissues and are responsible for the distribution of gases: e.g., hemoglobin in vertebrate blood, hemocyanin in molluscs, and myoglobin in striated muscle. Other emphores are used to protect living systems from infections and toxins (e.g., antibodies); others are used for transportation of metals (e.g., ceruloplasmin for copper and transferrin for iron), still others stabilize tissue levels of hormones and vitamins (e.g., thyroid binding globulin and intrinsic factor for vitamin $B_{12}$). Other emphores are used for the construction of proteins from their constituent amino acids (e.g., transfer RNA and sub-units of the ribosome) and for ultimate control of DNA (e.g., the repression or activation of genetic operons). These further emphores can be employed in systems wherein a molecular species sensed is not a small molecule (i.e., $\leq 100$ Daltons) as above but also in a system wherein a molecular species sensed comprises macromolecules (i.e., $\geq 100$ Daltons), to which they bind (e.g., antigens, Fe, Cu, CEA, vitamin $B_{12}$, thyroid hormone, DNA).

In such a large molecule detector said material 1 contains antibodies with specificity for the large molecule of interest. The antibodies are taken from the group consisting essentially of immunoglobin classes A, G, M, D and E. In such a detector, the means for detecting again may comprise optical means operable to detect any changes in the optical density of the material, the antibodies being specific for a particular antigen and being immobilized alone or with dyes and/or transition elements in a layer to yield a material wherein the optical density at a given wavelength changes with the binding thereto of the particular antigens (e.g., carcinoembryonic antigen, ceruloplasmin, components of B-streptococcal wall, human chorionic gonadotrophin (HCG), thyroid binding globulin, thyroid hormone, insulin, parathormone, etc.).

Figure 7:
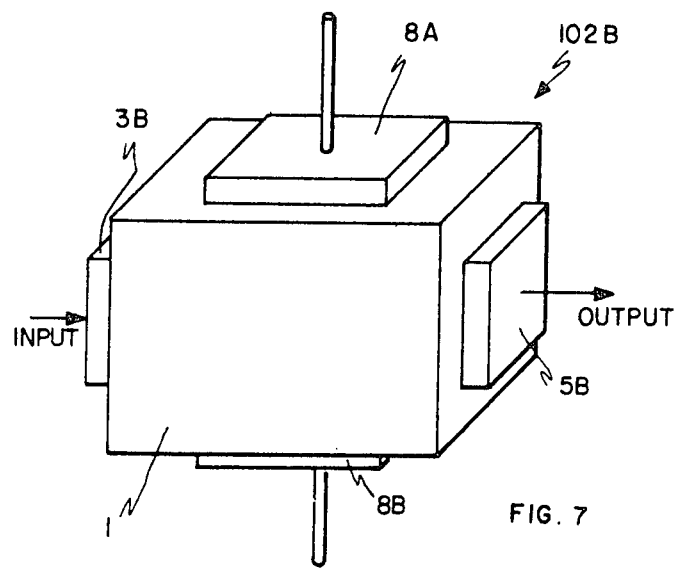
FIG. 7 shows a molecule detector, like the detector of FIG. 1, but employing transducers that differ from the optical radiation source and radiation sensor of FIG. 1.

The above explanation is made with reference to the preferred embodiment of the molecule detector apparatus which uses light as a sensing ingredient as well as a mechanism to enable the reset aspects. It should be noted that changes in other properties of the material 1 can be sensed, as well. Thus, with reference to FIG. 7, a molecular species detector 102B is shown again comprising a material 1 with electrodes 8A and 8B serving the same purpose as before; again an ion exchange membrane is used, but is not shown in FIG. 7. The elements shown as 3B and 5B in FIG. 7 are transducers, the first being an input transducer and the second being an output transducer. Thus, if the transducer 3B is an acoustic transducer that introduces high frequency phonons (see U.S. Pat. No. 3,871,017, Pratt, Jr.) to the material 1, which phonons are received by the sensor transducers 5B, changes in the intensity of the received phonons can be used as an indication of changes in the material 1 because of the presence of the molecule-of-interest in the environment and changes in the phonon intensity indicate the partial pressure of the molecule-of-interest. Also, injection of appropriate high frequency phonons in combination with an appropriate electroactive mediator in the material 1, serves to enhance charge carrier transfer thereto.

Also, the transducers 3B and 5B can be respectively means for introducing a magnetic field to the material 1 and magnetic sensor and the material 1 can be one whose magnetic properties change in the presence of the small molecule of interest and in proportion to the partial pressure of that molecule. For example, the $Fe^{++}$ in the hemoglobin detector is magnetic and the magnetic properties of the material 1 in such detector change in response to $O_2$, the environment in this case being diamagnetic. Or the transducers 3B and 5B can be electrical.

A practical embodiment of a detector device that may be fabricated is shown at 102A in FIG. 2 comprising a metal or plastic cap 10, an oxygen permeable membrane 9A, and an oxyemphore composition or material 1. Conductors 12 and 13 connect to the electrodes 8A and 8B, leads 14 and 15 connect to the LED 3 and the sensor 5. The electrical, optical and diffusive axes in the device 102A are the z, x and y axes, respectively, and represent in the systems herein disclosed, the electron flow direction, the light propagation direction and the diffusive path for the molecular species, respectively.

The device 102A can be constructed within a transistor header. The oxygen permeable membrane 9A covers the otherwise enclosed oxyemphore material 1 and preserves it from contamination. In an operating system, oxygen diffuses along the diffusive axis; radiation from the embedded LED is directed along the optical axis to the embedded sensor which can be a back-biased LED, as before. To reset the device, current flows into the conductor 12 to the electrode 8A, the material 1, the electrode 8B to the conductor 13 which is ground G (which is a common return path for all circuits here and in FIG. 3). A temperature sensor 17, energized through conductor 16 to ground G, sends messages to the master controller 7 in FIGS. 1 and 3 along a conductor 18. The device 102A can be calibrated in known ways using gases or the like having known partial pressures (see, for example, U.S. Pat. No. 3,826,920, Woodroffe et al); it is sensitive to temperature changes; hence the temperature sensor 17 is employed to compensate for changes in temperature.

Figure 3:
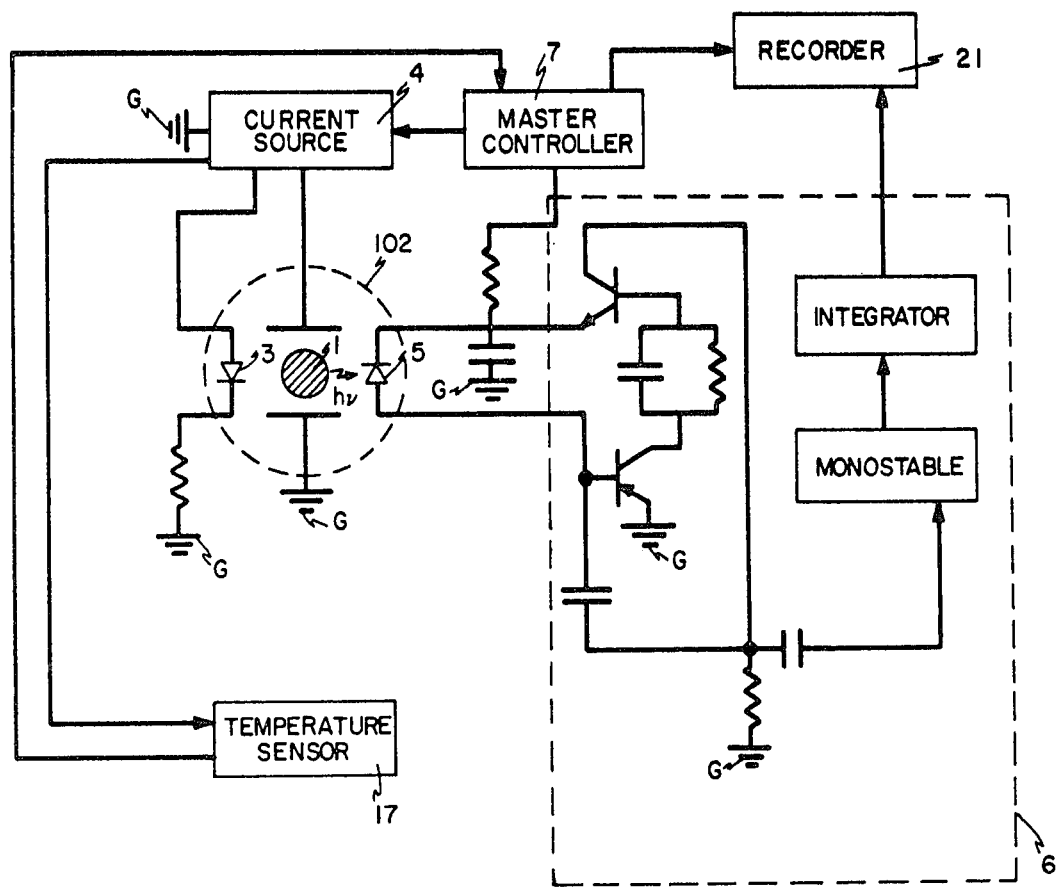
FIG. 3 shows, schematically and partly in block diagram form, a detector like the detector in FIG. 2, and pulse-interval-modulated analyzing circuitry to provide an indication of the partial pressure of a molecular species of interest in the environment about the detector.
Figure 4:
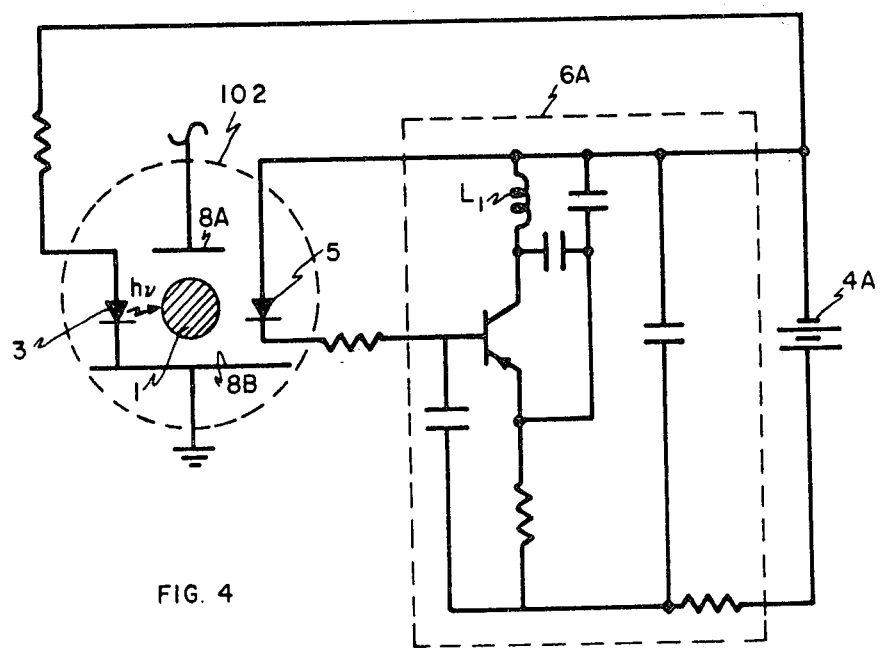
FIG. 4 shows schematically a system wherein the analyzing circuitry differs from that in FIG. 3 (i.e., the circuitry of FIG. 4 is frequency modulated), but the detector is similar to that of FIG. 3.

The circuit shown in some detail in FIG. 3 is one that the inventor has used to detect partial pressures in gases; it is shown mostly for enabling purposes and need not be explained in great detail. The circuitry in FIG. 4 is particularly adapted to in vivo uses; the inductance labeled $L_1$ can serve as an antenna to provide weak RF signals that can be picked up and interpreted by a small receiver (not shown) on a person's wrist, for example.

In said accompanying writing there are described devices built within dual-in-line packages wherein a material, like the material 1, is placed within said packages and between the LEDs. An ion exchange membrane is used (for purposes discussed elsewhere herein); and a platinum mesh is employed to define the electrical axis. The whole of the active part is embedded in an epoxy (Tracon 2113) which is a transparent, insulating and hydrophobic substance.

Figure 6:
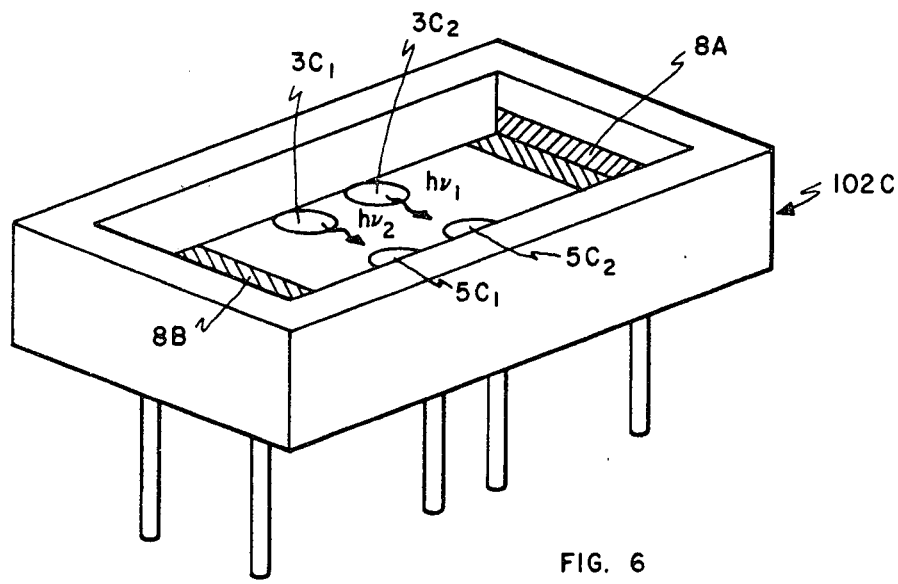
FIG. 6 is an isometric view, greatly enlarged, of a molecular species detector having two radiation sources and two sensors, but, for clarity, the material between the sources and the sensors and other parts are omitted.

In the molecule detector labeled 102C in FIG. 6, the material 1 is omitted to simplify the figure, as is a cover like the cover 9A in FIG. 2. Two radiation sources $3C_1$ and $3C_2$ and two radiation sensors $5C_1$ and $5C_2$, respectively, are included in the detector 102C.

The detector 102C in FIG. 6 is a diagrammatic and enlarged view of a detector that embodies the present invention and is a modification of a detector type that was built and tested. A fourteen lead hybrid dual-in-line package (Packing Unlimited CN5755) was used as a base upon which to construct the detector. Following an ultrasonic wash for one minute in distilled water, bonds were made between the terminals entering the packing and platinum mesh electrodes as well as red LEDs. The platinum mesh and the LED leads were soldered with an iridium alloy solder and flux. The units were later washed, again ultrasonically, photographed, and checked for continuity and independent working of each LED (two each, in three packages). Later the unit was tipped at an angle by inserting some of the leads into clay. Epoxy (Tracon 2113) was poured into the package in two stages separated by two days to form a channel bounded by platinum mesh and two light emitting diodes.

A much smaller and more compact arrangement than that in FIG. 6 can be achieved by using semiconductor fabrication techniques already well known. Mesas are fabricated by etching a chip of GaAsP/GaAs. At high temperature zinc (or tellurium, etc.) is made to diffuse into the mesas creating "p" regions. P-n junctions are then formed. If a groove is then cut, two p-n junctions with a common base are constructed; by then pouring a transparent, electrically insulating layer (as Tra-Con 2113), a barrier will be formed between the monolithic sensor and its (to-be-poured) hemogel (i.e., hemoglobin entrapped in gelatin). Electrical attachment to the p and n regions is obtained at the ends of the monolithic device thereby fabricated.

Figure 5:
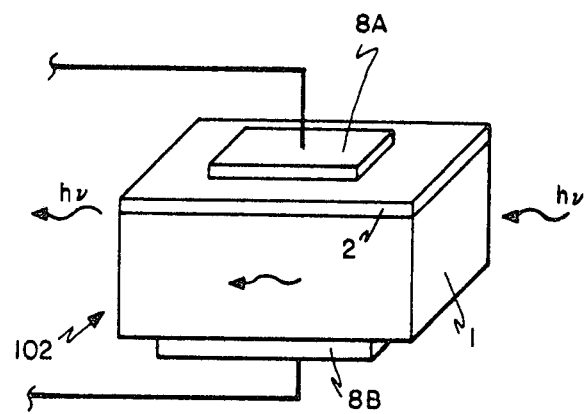
FIG. 5 is an isometric view of the portion of a detector, like the detector of FIG. 1, and is intended to emphasize the electrodes and an ion exchange membrane.

Previous mention is made of the use of an anion exchange membrane in the systems herein disclosed. With reference to FIG. 5, the anion exchange membrane, again designated 2, is in electrical contact with the electrode 8A and it affects the system in this way: in the absence of the membrane 2 there will be a buildup of oxidized material in the vicinity of the anode. With the membrane 2 present, reduction occurs across the bulk of the material 1.

The resetting concept disclosed herein can be used in other molecule detecting systems such as, for example, the system disclosed in U.S. Pat. No. 3,873,267 of the present inventor, but it can be used in other systems, too, as now explained, in connection with a system wherein enzymes or other catalysts are employed for chemical synthesis.

In the chemical synthesizing system shown schematically at 104 in FIG. 8, a substrate S passes either by gravity feed (or by force feed through a side port) through an enzyme or other catalytic core material 20 to provide as a product P (e.g., $NH_3$) in a chemical synthesis process that is widely known and used: the process in FIG. 8 is represented by the expression, substrate + enzyme → substrate − enzyme complex → product-enzyme complex → product + enzyme.

In the course of such synthesis, the enzyme may be subject to deterioration due to desiccation and due to changes incurred by the chemical synthesis process, as well as to oxidation, the latter being transition metal oxidation and/or sulfhydryl group oxidation; and the enzyme core 20 must be periodically upgraded. All forms of deterioration are ameliorated in the system in FIG. 8 wherein the enzyme material 20 that has become oxidized is reduced by introducing electrons thereto in the manner before discussed. The anode in FIG. 8 is marked $8A_1$ and the power source is a battery 40 (an anion exchange membrane is used in the system 104, as before, but is not shown). An electroactive mediator is added to the enzyme or other catalyst 20, as before, to facilitate charge transfer. In FIG. 8, the process occurs within a tubular reaction member 21 which may be glass or plastic, for example; the substrate is introduced through entrances 22A and 22B to the reaction member 21. The substrate S reacts with the enzyme contained in the material 20 (i.e., the material 20 is an appropriate enzyme plus an electroactive mediator, plus any required antidessicants, etc., as before, but the enzyme is the active part as far as the substrate is concerned) to form the product P which diffuses through the walls of tubes 23 (which walls are permeable to the product but not the material 20) and are removed from the system at the top and/or bottom as shown. In FIG. 8, the tubes 23 are shown at the top of the figures as open ellipses to represent hollow tubes, the elongate members $8B_1$ are shown as solid ellipses to distinguish them from the tubes 23, the members $8B_1$ being merely solid conductors that serve as cathodes throughout the length of the system 104. The two tubular members marked 25, and having dots at the upper ends of each to distinguish them from the cathodes $8B_1$ and the tubes 23, are lossy light pipes that receive light from a light source 24 and deliver it to the material 20 to irradiate the same for the reset purposes before discussed. A phonon generator 26 can be used to augment the light source 24 and light pipes 25. The generator 26 is intended to represent phonon generating transducers that may be embedded in the material 20 as well as appropriate energizing means.

The system labeled 104A in FIG. 9 is coaxial. A substrate S is introduced at the top of the system into a tube 23A of the system, it moves downward under the pull of gravity, it diffuses radially through the walls of the tube 23A outward into an annular region occupied by a material again marked 20 that comprises an enzyme or other catalyst, a product P is formed; the product P diffuses into the tube 23A and out of the system as before. The material 20 is periodically reset to counteract deterioration by passing a current between an anode $8A_2$ and a mesh cathode $8B_2$. Details of the interior anode, cathode and an anion exchange membrane are omitted; however, it should be noted that the electric field in FIG. 9 is transverse to the axis of the system, that is, the field lines are radial in the system 104A. The walls of the tubes 23A are impermeable to the material 20.

Figure 10:
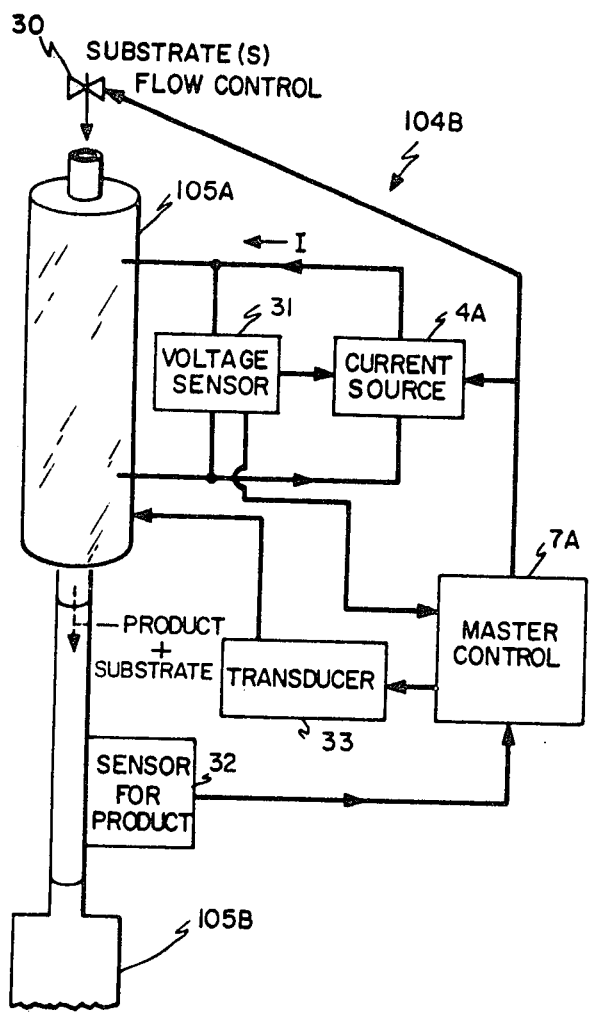
FIG. 10 shows a plurality of sections, like the section of FIG. 9 in tandem and, it shows, schematically, associated system elements.

The system shown at 104B in FIG. 10 is a serial system comprising two (or more) sub-systems 105A, 105B ... in tandem. Substrate S is introduced at the top of the system and a product exits from the bottom. The subsystem 105A is shown with control apparatus inluding a master controller 7A (which may be or may include a microprocessor) that serves to direct the various system functions which include substrate flow control through a valve 30. A sensor 32 notes product flow levels and, when the level of product flow drops below some predetermined level (which ordinarily will occur because of deterioration of the enzyme or other catalyst in the system), the master controller 7A energizes a current source 4A to introduce charge carriers into the enzyme or other catalyst, as before. The master controller 7A can also close the valve 30 to stop substrate flow. A voltage sensor 31 notes when the enzyme or other catalyst is renewed; it then turns off the current source 4A and/or sends an appropriate message to the master controller 7A. The subsystems 105B . . . can be similarly served. A transducer 33 introduces photons and/or phonons for the purposes previously discussed. In the tandem system 104B emission from the first and any intermediate stage is used as substrate for the next stage; and the emission from the last stage is the final product.

Figure 11A:
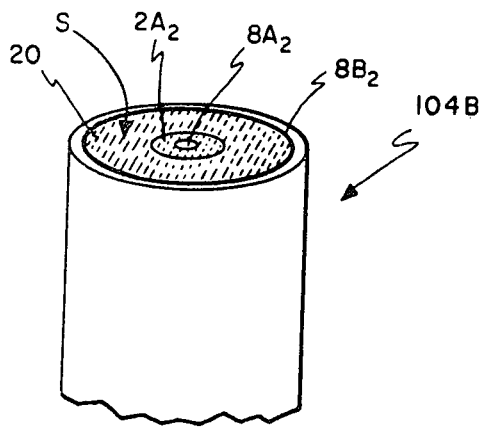
FIGS. 11A and 11B are partial isometric views of modifications of the section in FIG. 8.
Figure 11B:
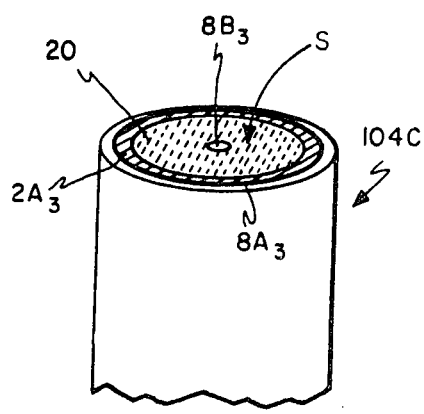

The systems shown respectively at 104B and 104C in FIGS. 11A and 11B are modifications of the system 104. The material is again marked 20 in these two systems and again is an enzyme or other catalytic material plus an electroactive mediator, etc. The material 20 occupies an annular space between anodes $8A_2$ and $8A_3$ and cathodes $8B_2$ and $8B_3$, respectively. The electric field lines in FIGS. 11A and 11B are radial; the substrate is introduced at the top of the material 20 in the two figures and flows downward by gravity feed. In the usual system the charge carriers injected are electrons to reduce the enzyme which has been oxidized in the course of catalysis. The anion exchange membrane in FIGS. 11A and 11B are marked $2A_2$ and $2A_3$, respectively.

The system marked 104D in FIG. 12 is a schematic representation of immobilized-enzyme, electrode-reduction-apparatus for forming ammonia from nitrogen. The substrate, nitrogen gas $N_2$, is introduced at the top, and the product, $NH_3$, leaves at the bottom, as shown. The material labeled 20A includes an azoemphore (i.e., a nitrogen binding material) which uses molybdenum and iron as its active elements, a gelatin binder, methylene blue as the electroactive mediator and a phosphate buffer. Currents through the composite 20A serves to renew the same; an anion exchange membrane 2A renders electroactive the region between the membrane 2A and the cathode marked $8B_5$, for such purposes. The anode in FIG. 12 is designated $8A_5$. The horizontal electric field between the anode $8A_5$ and the cathode $8B_5$ is marked $E_H$; periodically the field $E_H$ is removed and a vertical electric field $E_V$ (by electrodes not shown) is applied to move the ammonium within the system downward at a faster rate than would occur by gravity alone. A cation exchange membrane 35 serves a purpose similar to the membrane 2A, for the field $E_V$.

Figure 13:
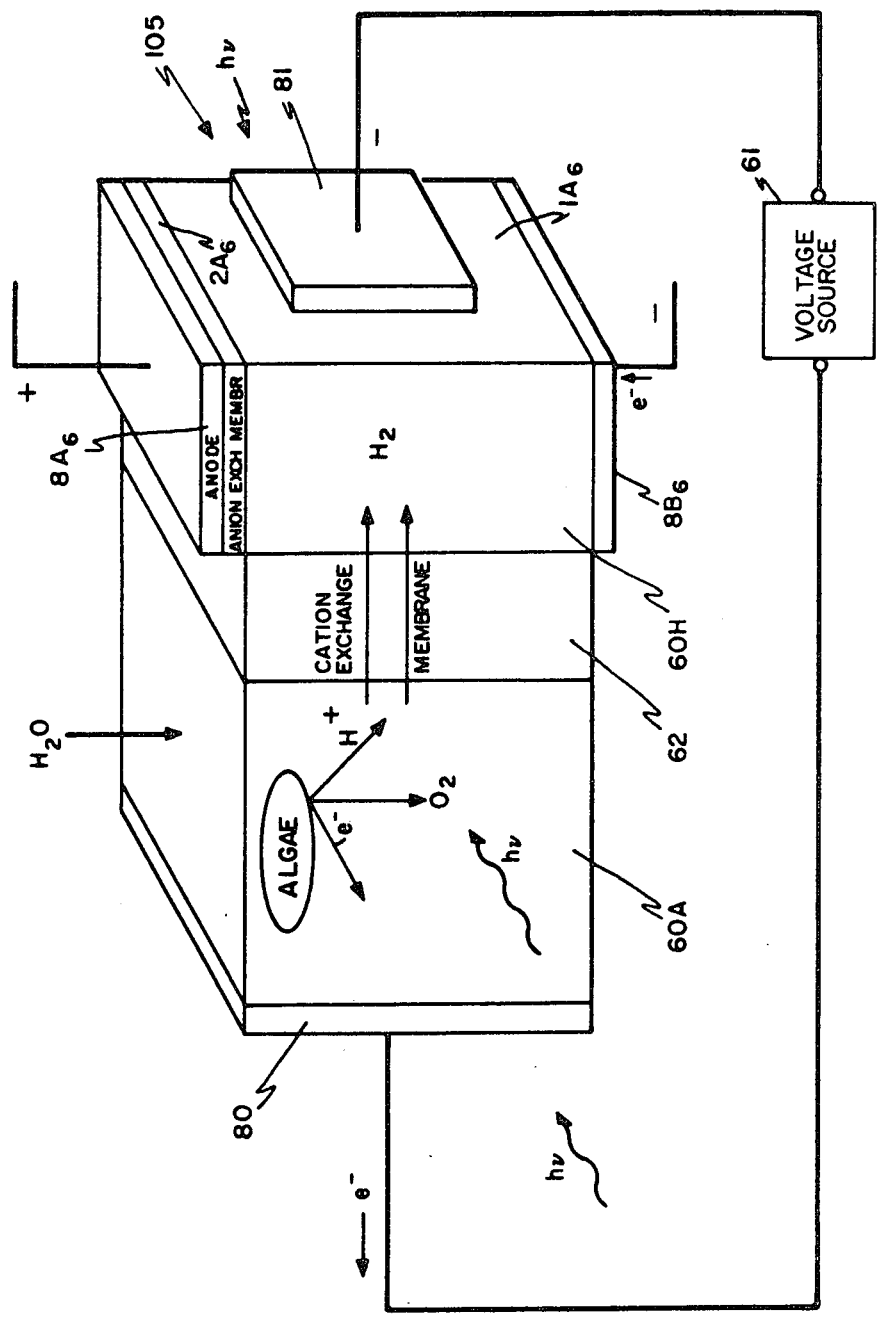
FIG. 13 is a schematic representation, partly block diagram in form, of a system wherein solar radiation under controlled conditions is employed to produce protons ($H^+$), wherein the protons convert to $H_2$, and wherein the material wherein the $H_2$ is formed is periodically reset.

The resetting feature above described also has use in the systems described in a journal article in *The Sciences*, October 1975, pp. 25-30, entitled "A Source of Self-Sufficiency," (Gorman); the article describes a photosynthesis process for producing hydrogen and an organic solar cell. The present teaching is concerned with rejuvenating the material in each system, as now explained with reference to FIG. 13 which shows a system 105 for the production of hydrogen gas from $H_2O$ and using light energy. (The chlorophyll in the organic solar cell described in the Gorman article can similarly be reset.) The system 105 comprises electrodes 80 and 81 connected across a voltage source 61 that applies a voltage ($\sim 1.0$ volt) across a material 60A containing algae or extracts of algae, as shown; $H_2O$ is introduced into the system 105 as is, also, light (hv) to activate the active components of the algae in a photosynthesis process. The products are $O_2$, protons ($H^+$) and electrons ($e^-$), as shown. The protons are pulled through a cationic exchange membrane 62 by a voltage of the source 61 into a material $1A_6$ that contains hydrogenase, an electroactive mediator, etc., and which deteriorates over time; periodically the material $1A_6$ is reset and, in the reset process, is subjected to light at an appropriate frequency similar to that used in hemoglobin rejuvenation. To reset, the voltage source 61 is disconnected from the system and a current source is connected between electrodes $8A_6$ and $8B_6$, as before, and light of appropriate frequency is shown upon the material $1A_6$. An ion exchange membrane $2A_6$ is employed. $H_2$ gas is formed in the entire bulk of the material $1A_6$. If the cation exchange membrane 62 is thin enough, the protons will diffuse therethrough without need of the voltage source 61.

Further modifications of the invention herein disclosed will occur to persons skilled in the art and all such modifications are deemed to be within the spirit and the scope of the invention as defined by the appended claims.

What is claimed is:

1. In a process wherein a chemical change is wrought upon a material as a consequence of it having been subjected to a reaction or reactions, which chemical change is an unwanted chemical deterioration resulting from a reversible reaction which can be counteracted by introducing appropriate charge carriers, electrons or holes, into the electronic states of said material, the further steps of adding small amounts of an electroactive mediator to the material to facilitate the charge carrier transfer to said electronic states, the resulting material being a matrix material and the electroactive mediator, said matrix material containing an inorganic catalyst used to effect the chemical reaction in which changes in character in the course of the chemical reaction are due to the environment within which the process occurred, introducing photons to the resulting material, the electroactive mediator being one which permits, in the presence of said photons, charge carrier transfer to the resulting material at an applied electric potential difference that is below the electrolysis potential of the resulting material, and applying an electric potential across the resulting material to inject appropriate charge carriers into the resulting material and into the electronic states thereof to counteract the unwanted chemical deterioration and cause the material to revert to a desired state.

2. A process as claimed in claim 1 wherein said electroactive mediator is taken from the group consisting essentially of dyes, quinones, free transition metals and other molecules with conjugated $\pi$-electron systems as well as other elements and complexes with $d^-$ and $f^-$ electrons capable of moving between two or more electronic states.

3. A process as claimed in claim 1 wherein the electroactive mediator is one which permits the charge transfer in the presence of photons of a narrow range of frequencies and in which the photons introduced are within that range.

4. A process as claimed in claim 1 wherein said deterioration is oxidation and wherein the reversion to a desired state is effected by reduction of the matrix material by introducing holes to said electronic states.

5. A process as claimed in claim 1 wherein said reversible deterioration is reduction and wherein the reversion to a desired state is effected by oxidation of the matrix material by introducing electrons to said electronic states.

6. A process as claimed in claim 1 wherein the electric potential is maintained for a time $\tau_R$, wherein $$\tau_R \simeq 9.7 \cdot 10^{10} \frac{[\Sigma]}{K \cdot \eta_R},$$

wherein $\Sigma$ is the molar sum of all oxidized constituents in said resulting material and k is electric current in microamperes.

7. A process as claimed in claim 6 wherein $\tau_R < \tau_o$, $\tau_o$ being the characteristic time of oxidation.

8. A system that comprises, in combination: material means that is subjected to a reaction or an environment which effects or tends to effect deterioration thereof by virtue of chemical processes, which deterioration is caused by a reversible reaction which can be counteracted by introducing appropriate charge carriers into the electronic states of said material means, said material means containing small amounts of an electroactive mediator to facilitate introduction of the charge carriers into the electronic states of said material means, said material means containing an enzyme used to effect the chemical reaction or reactions; means to contain the enzyme; means permitting a substrate to come in contact with the enzyme to produce a product; porous means permeable to the substrate and to the product to enable the product to be removed from the region of the enzyme; means to subject the material means to an electric field of sufficiently high intensity to counteract said deterioration and cause the material means to assume or to retain a desired state by the introduction of said charge carriers to said electronic states and yet sufficiently low in intensity and sufficiently high in efficiency that no substantial electrolysis occurs; and means to direct electromagnetic radiation upon the material means to enhance the effect of the electric field in introducing the charge carriers to the electronic states.

9. A system as claimed in claim 8 that further includes anion exchange membrane means that serves to affect the electric field profile, thereby permitting bulk change of said material.

10. A system as claimed in claim 8 wherein said material is a composite material that contains small amounts of said electroactive mediator which permits and enhances charge transfer to said material means in the presence of the electric field and the presence of phonons within a range of frequencies and which the last-named means is adapted to direct phonons in said range into said material means.

11. A system as claimed in claim 8 wherein said material means contains transition metal composites which bind other molecules.

12. A system as claimed in claim 8 wherein said means to subject comprises electrode means and electrical power source means connected to energize the electrode means.

13. A system as claimed in claim 12 in which the means to direct electromagnetic radiation upon the material is adapted to irradiate the electrode means as well.

14. A system as claimed in claim 8 that comprises an outer tube and an inner tube nested and coaxially disposed within the outer tube, with a space therebetween, the enzyme being disposed in said space, the inner tube being operable to receive a substrate and being permeable to the substrate, the substrate thus passing through the inner tube to the enzyme in said space to produce a product, the inner tube being porous also to the product which diffuses back into the inner tube, said electric field being a radial field in the space between the two tubes.

15. A system as claimed in claim 14 that further includes a tubular ion exchange membrane disposed in the space between the inner tube and the outer tube.

16. A system as claimed in claim 14 having means to create a longitudinal electric field along the inner tube to facilitate entry of the substrate into the system and or to facilitate extraction of the product.

17. A system as claimed in claim 16 having means to introduce the enzyme into said space.

18. A system as claimed in claim 17 wherein the means to subject the material means to an electric field is a source of electric potential, that further includes means to sense the electric potential that appears across said space and that further includes feedback connections so that when the regeneration is complete the electric potential is terminated.

19. A method of controlling the aging process of a toxin subject to aging, which aging results from a reversible reaction that can be counteracted by introducing appropriate charge carriers into the electronic states of said toxin, that comprises: introducing methylene blue as an electroactive mediator to the toxin to facilitate the introduction of charge carriers to the electronic states thereof; irradiating the toxin further to facilitate the introduction of charge carriers to the electronic states thereof; and applying an electric potential across the toxin to introduce the charge carriers to the material and into the electronic states thereof, and wherein photons in the red region of the electromatic spectrum are introduced to the toxin to enhance said charge carrier transfer to said toxin.

20. A method as claimed in claim 19 wherein the aging process is accelerated by changing said charge carrier.

21. A process for producing $H_2$ gas from $H_2O$ that includes introducing $H_2O$ to an algae system in the presence of light, which algae system, in the presence of light, separates molecules of $H_2O$ into $O_2$ molecules, protons ($H^+$) and electrons ($e^-$), drawing the protons ($H^+$) into a material that is operable to add electrons ($e^-$) to the protons ($H^+$) to produce $H_2$ gas, which material is subject to chemical deterioration that can be counteracted by introducing appropriate charge carriers into the electronic states of said material, the further steps of adding an electroactive mediator to the material, the electroactive mediator being one which, in the presence of photons, permits charge carrier transfer to said electronic states at an applied potential that is below the electrolysis potential of the resulting material, introducing photons to the resulting material, and applying an electric potential across the material to introduce charge carriers thereto.

22. A process for producing $H_2$ gas from $H_2O$ that includes the steps of introducing $H_2O$ to an organic system in the presence of light, which organic system, in the presence of light, separates molecules of $H_2O$ into $O_2$ molecules, protons ($H^+$) and electrons ($e^-$), drawing the protons ($H^+$) into a material that contains hydrogenase and an electroactive mediator, which material is operable to convert the protons ($H^+$) to $H_2$ gas, said material being subject to reversible deterioration over time, and periodically applying an electric potential across the material to introduce charge carriers into the material, which charge carriers serve to counteract the reversible deterioration and reset the material.

23. In a system for producing $H_2$ gas from $H_2O$, an organic solar cell comprising an organic material that in the presence of solar radiation separates molecules of $H_2O$ into $O_2$ molecules, protons ($H^+$) and electrons ($e^-$), cationic exchange membrane means that can pass the protons ($H^+$) therethrough, a further material that contains hydrogenase and an electroactive mediator positioned to receive the protons ($H^+$) after passage through the cationic exchange membrane means and operable to add an electron ($e^-$) thereto to produce the $H_2$ gas therefrom, said further material being subject to deterioration over time, and electronic power source means connected to inject charge carriers into the further material, which charge carriers serve, in the presence of light, to counteract said deterioration and reset the further material.

24. An organic solar cell as claimed in claim 23 wherein the cation exchange membrane means comprises a cation exchange membrane that is thin enough to pass the protons ($H^+$) therethrough without an external field applied thereacross.

25. An organic cell as claimed in claim 23 that includes voltage source means positioned to apply an electric potential across the organic material and the cationic exchange membrane means with appropriate polarity to cause the protons ($H^+$) to drift toward the cationic exchange membrane means and to diffuse through the cationic exchange membrane means into said further material.

26. An organic solar cell as claimed in claim 23 wherein the organic material contains algae.

27. An organic solar cell as claimed in claim 26, wherein the organic material contains extracts of algae.

28. An organic solar cell as claimed in claim 26 wherein the organic material contains chlorophyll.

29. An organic solar cell as defined by claim 23 wherein the $H_2$ gas is formed in the bulk of the further material and wherein the power source means comprises spaced electrodes positioned to inject said charge carriers into the bulk of the further material, there being an ion exchange membrane interposed between one of the electrodes and said further material.

30. An organic solar cell as defined by claim 29 wherein said charge carriers are electrons ($e^-$) directed into the bulk of the further material.

* * * * *